United States Patent [19]
Charmot et al.

[11] Patent Number: 5,356,713
[45] Date of Patent: Oct. 18, 1994

[54] MAGNETIZABLE COMPOSITE MICROSPHERES OF HYDROPHOBIC CROSSLINKED POLYMER, PROCESS FOR PREPARING THEM AND THEIR APPLICATION IN BIOLOGY

[75] Inventors: Dominique Charmot; Christine Vidil, both of Paris, France

[73] Assignee: Rhone-Poulenc Chimie, Courbevoie, France

[21] Appl. No.: 70,053

[22] Filed: Jun. 1, 1993

Related U.S. Application Data

[63] Continuation of Ser. No. 501,929, Mar. 30, 1990, abandoned.

[30] Foreign Application Priority Data

Mar. 31, 1989 [FR] France ................. 89 04231

[51] Int. Cl.$^5$ .................. B32B 5/16; G01N 33/553
[52] U.S. Cl. .................. 428/407; 252/62.54; 428/403; 436/526
[58] Field of Search ............. 252/62.54; 428/402.24, 428/403, 407; 436/526

[56] References Cited

U.S. PATENT DOCUMENTS

| | | | |
|---|---|---|---|
| 3,228,881 | 1/1966 | Thomas | 252/62.5 |
| 3,714,102 | 1/1973 | Reiss | 260/29.6 R |
| 3,843,540 | 10/1974 | Reimers et al. | 252/62.52 |
| 4,339,337 | 7/1982 | Tricot et al. | 252/62.54 |
| 4,358,388 | 11/1982 | Daniel et al. | 252/62.54 |
| 4,421,660 | 12/1983 | Solc nee Hajna | 252/62.54 |
| 4,454,234 | 6/1984 | Czerlinksi | 436/526 |
| 4,680,200 | 7/1987 | Solc | 427/213.34 |
| 4,695,392 | 9/1987 | Whitehood et al. | 436/526 |
| 4,948,739 | 8/1990 | Charmot et al. | 436/533 |
| 4,985,166 | 1/1991 | Leising et al. | 252/62.54 |
| 5,034,145 | 7/1991 | Leising et al. | 252/62.54 |

FOREIGN PATENT DOCUMENTS 3305149 12/1988 Japan.

Primary Examiner—D. S. Nakarani
Attorney, Agent, or Firm—Finnegan, Henderson, Farabow, Garrett & Dunner

[57] ABSTRACT

Magnetizable composite microspheres approximately from 0.05 to 10 μm in diameter, comprising a core of magnetizable particles and a shell of a hydrophobic crosslinked copolymer formed from a vinylaromatic monomer and a crosslinking emulsifying polymer. The microspheres are obtained by the pre-emulsification in water of a magnetic fluid composed of magnetizable particles dispersed in a vinylaromatic monomer and in a crosslinking emulsifying polymer, polymerization, separation of the magnetizable microspheres and optional redispersion in water. The microspheres are useful in biological applications.

9 Claims, 2 Drawing Sheets

MAGNETIZABLE COMPOSITE MICROSPHERES OF HYDROPHOBIC CROSSLINKED POLYMER, PROCESS FOR PREPARING THEM AND THEIR APPLICATION IN BIOLOGY

This application is a continuation of application Ser. No. 07/501,929, filed Mar. 30, 1990, now abandoned.

FIELD OF THE INVENTION

The present invention relates to magnetizable composite microspheres of hydrophobic crosslinked vinylaromatic polymers, as they are or in aqueous dispersion, tea process for preparing them and to their application, particularly in biology.

BACKGROUND OF THE INVENTION

It is known to prepare magnetizable beads (U.S. Pat. No. 4,339,337) ranging in diameter from 0.05 to 3 mm by the suspension polymerization of a vinylaromatic monomer in the presence of an organosoluble initiator, a suspending agent and a magnetizable charge which is dispersed in a solution of a non-water-soluble polymer in the monomer. The beads obtained contain magnetizable charges distributed in the polymer matrix.

It has also been proposed (U.S. Pat. No. 4,358,388) to prepare latices of magnetizable hydrophobic polymers by the homogenization of an aqueous solution of emulsifier and a dispersion of a magnetizable charge in an organic phase composed of an organosoluble initiator, all or part of the hydrophobic monomer and/or a water-insoluble organic compound, followed by polymerization. The latices obtained are composed of polymer particles approximately 0.03 to 5 µm in diameter containing magnetizable charges distributed in the polymer matrix, the charges tending to migrate to the periphery.

SUMMARY OF THE INVENTION

The instant invention provides composite microspheres composed of a core comprising magnetizable particles and a shell of hydrophobic polymer. Also provided is a process for preparation of these microspheres, and a method of use thereof.

DETAILED DESCRIPTION OF THE INVENTION

Figure 1:
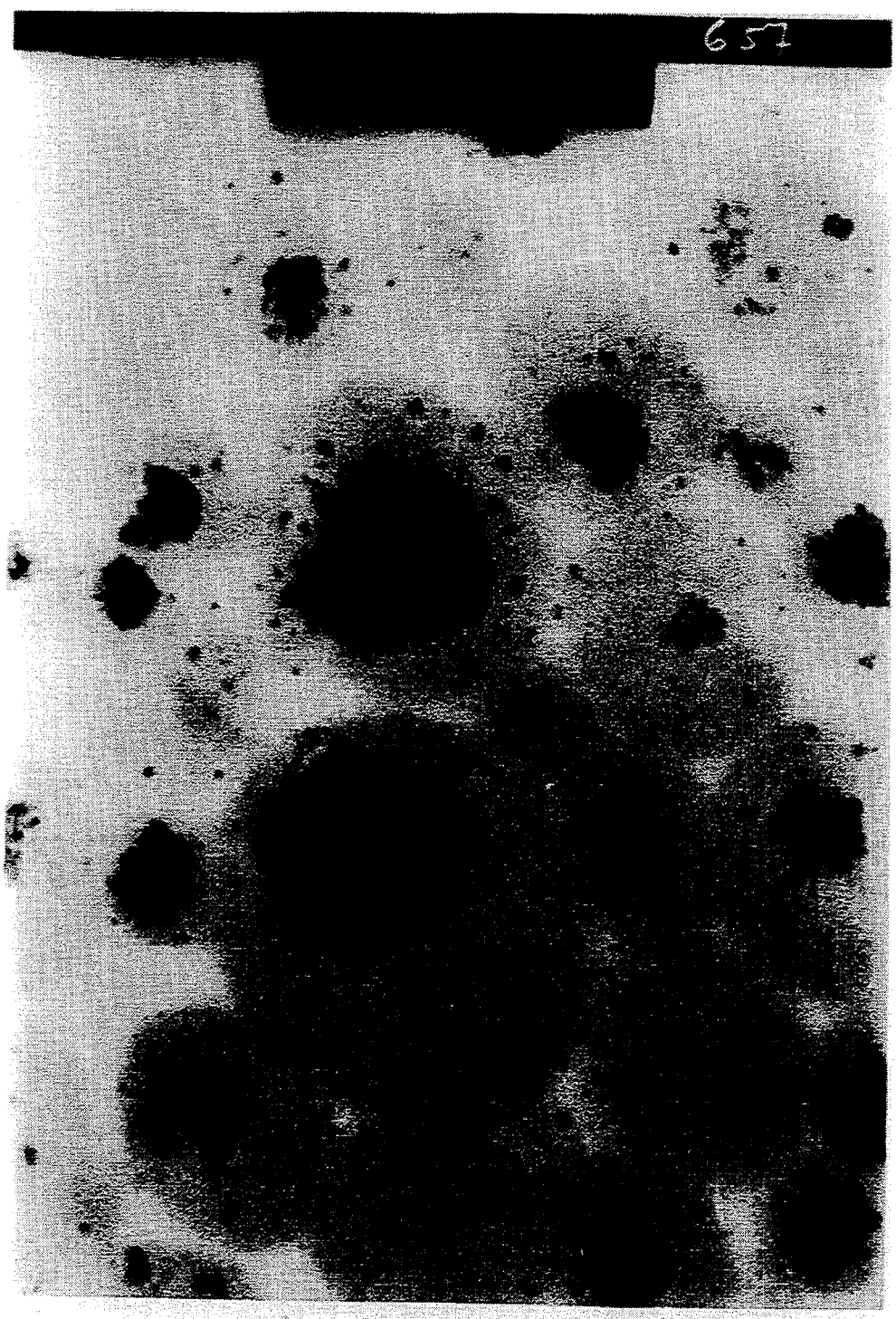
Figure 2:
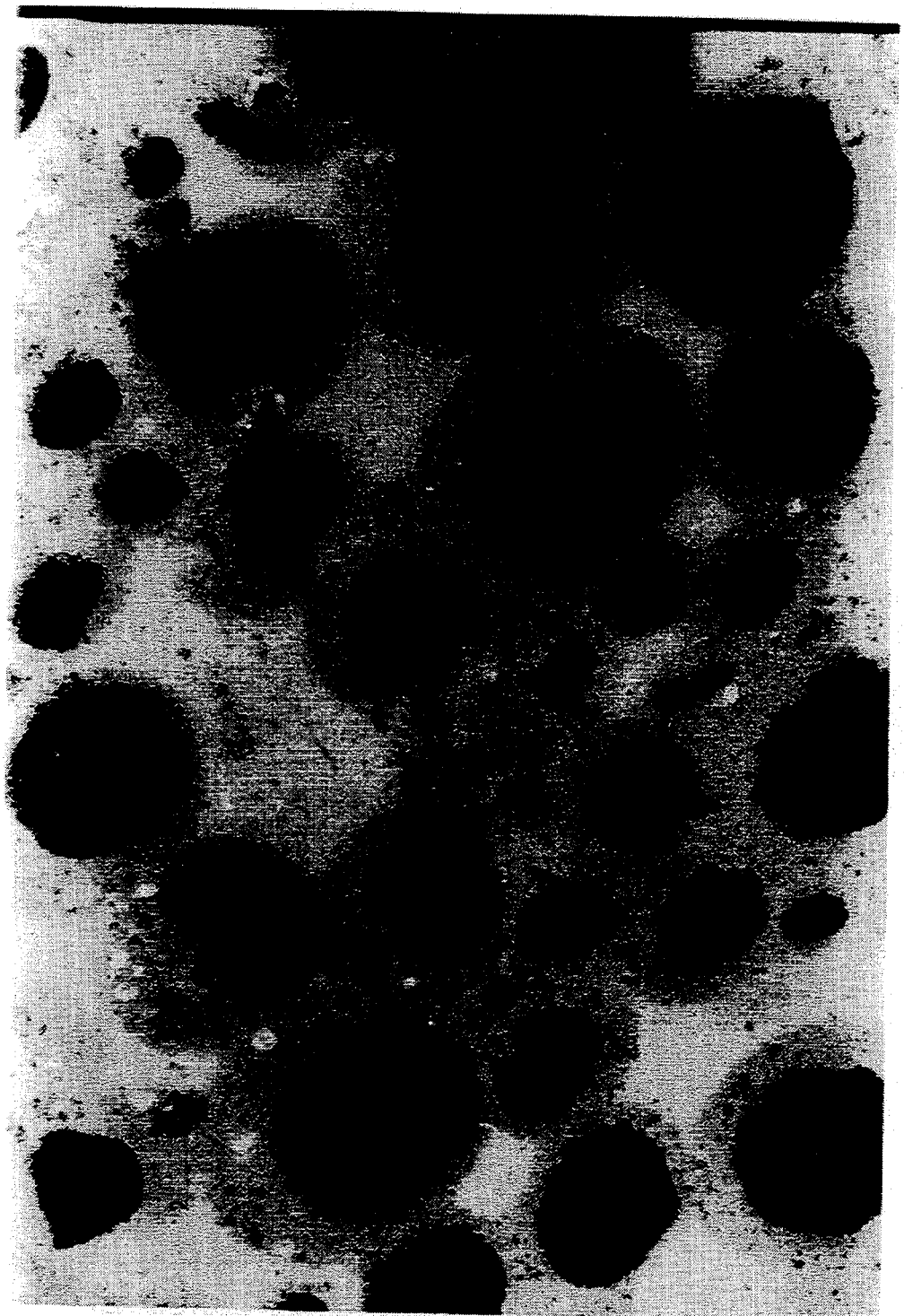

The instant invention provides magnetizable composite microspheres of hydrophobic crosslinked vinylaromatic polymer which are approximately from 0.05 to 10 µm, preferably from 0.1 to 5 µm, in diameter, and which comprise:

(1) a core comprising magnetizable particles less than $300 \times 10^{-4}$ µm, preferably from $50 \times 10^{-4}$ to $120 \times 10^{-4}$ µm, in diameter; and (2) a shell consisting essentially of a hydrophobic crosslinked copolymer formed from at least one hydrophobic vinylaromatic monomer and at least one polyethylenically unsaturated emulsifying polymer which is soluble in the vinylaromatic monomer(s) and capable of crosslinking with the vinylaromatic monomer(s).

The magnetizable particles are concentrated in the core of the microspheres of the instant invention. Preferably, the core essentially consists of the magnetizable particles.

Exemplary materials which may constitute the magnetizable particles forming the core of the microspheres include magnetite, haematite, chromium dioxide, ferrites such as manganese, nickel and manganese-zinc ferrites, alloys of cobalt, nickel, gadolinium and samarium-cobalt. Preferred materials are magnetite and haematite.

The quantity of magnetizable particles forming the core preferably corresponds to approximately 0.5 to 70%, most preferably to approximately 15 to 60%, of the weight of the magnetizable composite microsphere.

The shell of the composite microsphere consists essentially of hydrophobic crosslinked copolymer, and is, relative to the core, substantially free of magnetizable particles. Most preferably, the shell is entirely free of the magnetizable particles.

Exemplary vinylaromatic monomers include styrene, alpha-methylstyrene, ethylstyrene, tert-butylstyrene, vinyltoluene, and such similar monomers.

The vinylaromatic monomers may be present alone or mixed with one another in any proportion, or, alternatively, mixed with another water-insoluble copolymerizable monomer which may constitute up to 50% of the mixture. Exemplary water-insoluble copolymerizable monomers include diene compounds such as butadiene and isoprene; alkyl acrylates and methacrylates in which the alkyl group possesses 3 to 10 carbon atoms; and esters of ethylenic acids possessing 4 or 5 carbon atoms and alkyl radicals possessing 1 to 8 carbon atoms, such as: heptyl fumarate, octyl fumarate, methyl itaconate and ethyl itaconate.

From 0 to 5% by weight, relative to the monomer(s), of a crosslinking monomer such as, for example, divinylbenzene, vinylmethacrylate, mono- or polyalkylene(2–4C) glycol acrylates or methacrylates, triallyl cyanurate or condensates of unsaturated carboxylic acids and polyols such as, for example, trimethylolpropane acrylate and methacrylate, may also be present.

Exemplary emulsifying polymers crosslinking with the vinylaromatic monomer(s) include polyesters of alkylene glycol and unsaturated aliphatic and/or aromatic diacid, and carboxylated polymers of diolefins, having a weight average molecular mass approximately from 500 to 10,000, preferably from 1,000 to 5,000. Particularly preferred emulsifying polymers are polyesters of propylene glycol and maleic anhydride and polyesters of propylene glycol, maleic anhydride and phthalic anhydride.

The crosslinking emulsifying polymers preferably represent approximately from 3 to 15%, most preferably from 5 to 10%, of the weight of hydrophobic vinylaromatic monomer. The term "hydrophobic vinylaromatic monomer" denotes herein the group composed of hydrophobic vinylaromatic monomers, their comonomers and any crosslinking comonomers.

The magnetizable composite microspheres which form the subject of the invention may be presented as they are or in dispersion in water. The quantity of dispersed microspheres preferably corresponds to approximately 10 to 70%, most preferably 15 to 50%, of the total weight of the dispersion.

The present invention also provides a process for preparing the magnetizable composite microspheres. The process comprises the steps of:

(a) dispersing magnetizable particles less than $300 \times 10^{-4}$ µm, preferably from $80 \times 10^{-4}$ to $120 \times 10^{-4}$ µm, in diameter, coated with an approximately monomolecular layer of a non-water-soluble dispersant agent, in a mixture comprising at least one hydrophobic vinylaromatic monomer, at least one polyethylenically unsaturated emulsifying polymer which is soluble in the vinylaromatic monomer(s) and capable of crosslinking with the vinylaromatic monomer(s) and, optionally, an additional dispersant agent;

(b) introducing into the fluid obtained in step (a) an organosoluble polymerization initiator, and then subsequently pre-emulsifying the magnetic fluid thereby obtained in water; and (c) copolymerizing the ethylenically unsaturated compounds present in the medium.

It is preferred to separate the magnetizable microspheres formed from the non-magnetizable microspheres. Optionally, the magnetizable microspheres are then redispersed in water.

Hereinafter, "vinylaromatic monomers" will be understood to mean the group composed of vinylaromatic monomers, their comonomers and any crosslinking comonomers. The nature of these monomers, and the respective quantities in which they may be employed, have already been mentioned above. The crosslinking comonomers may be employed either at the dispersion step or at the pre-emulsification step, where they can then act as a solvent for the polymerization initiator. Also hereinafter, the term "copolymerizable ethylenically unsaturated compounds" will be understood to mean the group composed of the "vinylaromatic monomers" and the crosslinking emulsifying polymer.

The nature of the magnetizable particles has already been mentioned above.

Exemplary dispersant agents forming a non-water-soluble approximately monomolecular coating around the magnetizable particles include those compounds having a long hydrocarbon chain terminating in a polar group such as —COOH or —NH$_2$. Preferably, these dispersant agents are fatty acids or fatty amines containing at least 12 carbon atoms, most preferably $C_{18}$ fatty acids such as oleic, linoleic and linolenic acids.

The magnetizable particles coated with a dispersant agent may be prepared, for example, by peptization in the dispersant agent of magnetic particles obtained by the solgel method, dispersion in an organic carrier liquid (U.S. Pat. No. 3,843,540) followed by flocculation using a polar solvent of the ketone, ester or alcohol type and separation of the coated particles.

The proportion of magnetizable particles preferably represents from 0.5 to 60%, most preferably from 15 to 50%, of the weight of copolymerizable ethylenically unsaturated compounds.

The step of dispersing the magnetizable particles may preferably be carried out by gradual introduction, with stirring at a temperature of approximately 0° to 32° C., of the magnetizable particles coated with a non-water-soluble dispersant agent into the copolymerizable ethylenically unsaturated compounds. If appropriate, this step may be carried out in the presence of an additional anionic or cationic dispersant agent, for example, an agent selected from ethoxylated alkylaromatic phosphoric esters. The agent is preferably employed in the proportion of 3 to 15% of the weight of the copolymerizable ethylenically unsaturated compounds.

An organosoluble polymerization initiator is then introduced into the dispersion, optionally in the form of a solution in a small amount of vinylaromatic monomer or of one of its crosslinking or non-crosslinking comonomers.

The initiator is preferably employed in a quantity between approximately 0.1 and 10% by weight relative to the copolymerizable ethylenically unsaturated compounds.

Exemplary initiators include azonitriles such as azobisisobutyronitrile, azobiscyclohexanecarbonitrile; or peroxides such as benzoyl, dicumyl, di-tert-butyl, diacetyl, dioctanoyl, lauroyl, methyl ethyl ketone, capryloyl, 2,4-dichlorobenzoyl, parachlorobenzoyl peroxides; tert-butyl perpivalate, diethylperacetate, perbenzoate; di-tert-butyldiperphthalate; and 1,1-di(tert-butyldioxy)-3,3,5-trimethylcyclohexane.

The pre-emulsification step is preferably carried out by homogenization of the magnetic fluid obtained with water, at a temperature below the decomposition temperature of the initiator, using a vigorous stirring system such as a colloid mill, high pressure pump, vibration agitator, or ultrasonic apparatus, until an emulsion of droplets of magnetic fluid approximately from 0.03 to 10 $\mu$m, preferably from 0.1 to 5 $\mu$m, in size is obtained.

The pre-emulsification operation is preferably carried out at a pH approximately from 7 to 11.

The quantity of water present is preferably such that the aqueous dispersion of microspheres obtained after copolymerization contains from 10 to 65%, preferably from 10 to 30%, of its weight of microspheres.

If appropriate, an additional emulsifier may be present. The added emulsifier may be anionic, cationic or nonionic, and is preferably used in the proportion of 0.1 to 5% by weight relative to that of the ferrofluid, that is, the magnetic fluid, to be pre-emulsified.

Exemplary anionic emulsifying agents include fatty acid salts; alkali metal alkyl sulfates, alkylsulfonates, alkylarylsulfonates, alkylsulfosuccinates, alkylphosphates; alkyl sulfosuccinates; sulfonates of alkylphenolpolyglycol ethers; salts of alkylsulfopolycarboxylic acid esters; condensation products of fatty acids with oxy- and aminoalkanesulfonic acids; sulfated derivatives of polyglycol ethers; sulfated esters of fatty acids and polyglycols; and sulfated fatty acid alkanolamides.

Exemplary cationic emulsifying agents include alkylamines and their water-soluble salts and the soluble salts of alkylamines N-substituted with alkyl and/or alkylaryl and/or hydroxyalkyl radicals.

Exemplary nonionic emulsifying agents include fatty esters of polyhydric alcohols, fatty acid alkanolamides, poly(ethylene oxides), copoly(ethylene/propylene oxides) and oxyethylenated alkylphenols.

The polymerization operation is preferably carried out at a temperature of approximately from 30° to 130° C., most preferably from 50° to 85° C.. The operation may last approximately from 2 to 10 hours, and generally from 2 to 5 hours.

An aqueous dispersion of a mixture of magnetizable composite microspheres and microspheres not containing magnetizable charges ("blank" microspheres), whose diameter is approximately from 0.05 to 10 $\mu$m, generally from 0.1 to 5 $\mu$m, is thereby obtained. The content of magnetizable microspheres may represent from 20 to 90% by weight of the total quantity of microspheres. The greater the concentration of magnetizable charges in the microspheres, the greater the quantity of "blank" microspheres.

The separation of the magnetizable microspheres is preferably carried out by magnetization.

If desired, the separated magnetizable microspheres may be redispersed in water to obtain a dispersion preferably containing from 10 to 70% by weight, most preferably 15 to 50% by weight, of magnetizable composite microspheres.

The magnetizable composite microspheres, as they are or in aqueous dispersion, described above, may be used in biology for immobilizing, by adsorption or covalent bonding, biologically active substances, for example, proteins such as antibodies and enzymes; antigens; and medicinal products. Depending on the nature of the active substance, the products of the invention may be advantageously used in diagnostic tests (agglutination—"RIA" radioimmunoassay—"IRMA" immunoradiometric assay—"EIA" enzyme immunoassay), in affinity chromatography, as an enzymatic catalyst in biotechnology and as a cell culture support.

The examples which follow are given as a guide, and should not be considered as limiting the scope or spirit of the invention.

EXAMPLE 1

1st Step: Dispersion of the magnetic pigment

The following were introduced into 75.5 g of styrene:
8 g of Resin A 123 (polycondensates of propylene glycol and maleic and phthalic anhydrides, marketed by ORKEM); and
4 g of GAFAC RE 610 (mixture of phosphoric mono- and diesters of ethoxylated alkylaryl derivatives, marketed by GAF).

12.5 g of magnetic pigment, consisting of 10 g of $Fe_3O_4$ of average diameter on the order of $80 \times 10^{-4}$ to $120 \times 10^{-4}$ $\mu m$ subjected to the surfactant action of 2.5 g of oleic acid, were introduced gradually with stirring into the mixture obtained.

2nd Step: Pre-emulsification

A solution of 0.6 g of dioctanoylperoxide in 1.5 g of divinylbenzene was added to 40 g of the magnetic fluid obtained.

The organic phase obtained was introduced into 230 g of water brought to pH 10 by adding 1N potassium hydroxide, and dispersed in the aqueous phase using an ULTRA-TURREX homogenizer (drive motor T 45, dispersion shaft 45N, generator T 45/66, marketed by PROLABO).

The average diameter of the droplets obtained was on the order of 0.4 $\mu m$ (measurement using a CILAS 850 laser particle size meter, marketed by CILAS).

3rd Step: Copolymerization

The pre-emulsion obtained was polymerized in a 500 liter reactor at 80° C. for 4 hours under nitrogen. The medium was then cooled. During cooling, 50 ml of an aqueous solution containing 0.5% by weight of sodium lauryl sulfate were added.

The latex obtained was filtered off on a 5 $\mu m$ screen. The residual monomers were removed by stripping using a rotary evaporator.

The magnetizable microspheres were then separated using a magnet; their content represented approximately 65% of the total weight of microspheres.

The magnetizable microspheres had an average diameter on the order of 0.4 $\mu m$, and contained 18% of their weight of ferrite particles forming the core of the microspheres, as shown in FIG. No. 1, which is a photo showing a section of the microspheres seen in a transmission microscope; magnification 120,000.

EXAMPLE 2

The procedure of Example 1 was repeated, using the following quantities of the same reactants:

1st Step

| | |
|---|---|
| Resin A 123 | 6 g |
| GAFAC RE 610 | 4 g |
| Styrene | 60 g |
| Magnetic pigment | 30 g |

2nd Step

| | |
|---|---|
| Dioctanoyl peroxide | 0.7 g |
| Divinylbenzene | 1.5 g |
| Organic phase of the 1st Step | 40 g |
| Water, pH 10 | 200 g |

3rd Step

The polymerization conditions were identical to those of Example 1. 50% of the weight of the microspheres formed were magnetizable.

The magnetizable microspheres had an average diameter on the order of 0.6 $\mu m$ and contained 43% of their weight of ferrite particles forming the core of the microspheres, as shown in the photo of FIG. No. 2 (magnification 44,000).

What we claim is:

1. Magnetizable composite microspheres of hydrophobic crosslinked vinylaromatic polymer which are approximately from 0.05 to 10 $\mu m$ in diameter, and which comprise:
   (1) a core comprising magnetizable particles less than $300 \times 10^{-4}$ $\mu m$ in diameter coated with an approximately mono molecular layer of a non-water-soluble dispersing agent; and
   (2) a shell consisting essentially of a hydrophobic crosslinked copolymer formed from at least one hydrophobic vinylaromatic monomer and at least one polyethylenically unsaturated emulsifying polymer which is soluble in said vinylaromatic monomer(s) and capable of crosslinking with said vinylaromatic monomer(s), wherein said shell is substantially free from said magnetic particles relative to said core.

2. The microspheres of claim 1, wherein the weight of magnetizable particles forming the core represents approximately from 0.5 to 70% of the weight of said magnetizable composite microspheres.

3. The microspheres of claim 1, wherein said magnetizable particles are of magnetite or of haematite.

4. The microspheres of claim 1, wherein said crosslinking emulsifying polymer is a polyester of alkylene glycol and unsaturated aliphatic diacid, aromatic diacid or a mixture thereof having a weight average molecular mass approximately from 500 to 10,000.

5. The microspheres of claim 1, wherein said crosslinking emulsifying polymer represents approximately from 3 to 15% of the weight of hydrophobic vinylaromatic monomer.

6. An aqueous dispersion comprising the microspheres of claim 1.

7. The aqueous dispersion of claim 6, wherein the weight of dispersed magnetizable microspheres corresponds to approximately from 10 to 70% of the total weight of said dispersion.

8. The microspheres of claim 1, wherein said microspheres are approximately from 0.10 to 5 $\mu m$ in diameter.

9. The microspheres of claim 1, wherein the magnetizable particles are approximately from $50 \times 10^{-4}$ to $200 \times 10^{-4}$ $\mu m$ in diameter.

* * * * *